(12) United States Patent
Malkoch et al.

(10) Patent No.: US 12,023,411 B2
(45) Date of Patent: Jul. 2, 2024

(54) DENDRITIC NANOGEL CARRIERS AND METHOD OF PRODUCTION

(71) Applicant: POLYMER FACTORY SWEDEN AB, Stockholm (SE)

(72) Inventors: Michael Malkoch, Täby (SE); Surinthra Mongkhontreerat, Stockholm (SE); Oliver Andrén, Stockholm (SE); Randi Nordström, Uppsala (SE); Yuning Zhang, Sollentuna (SE)

(73) Assignee: POLYMER FACTORY SWEDEN AB, Stockholm (SE)

( * ) Notice: Subject to any disclaimer, the term of this patent is extended or adjusted under 35 U.S.C. 154(b) by 315 days.

(21) Appl. No.: 17/264,716

(22) PCT Filed: Aug. 13, 2019

(86) PCT No.: PCT/SE2019/050745
§ 371 (c)(1),
(2) Date: Jan. 29, 2021

(87) PCT Pub. No.: WO2020/036529
PCT Pub. Date: Feb. 20, 2020

(65) Prior Publication Data
US 2021/0299061 A1    Sep. 30, 2021

(30) Foreign Application Priority Data
Aug. 13, 2018    (SE) .................................... 1850975-2

(51) Int. Cl.
| | | |
|---|---|---|
| *A61K 45/06* | (2006.01) | |
| *A61K 9/06* | (2006.01) | |
| *A61K 9/51* | (2006.01) | |
| *B82Y 5/00* | (2011.01) | |
| *B82Y 30/00* | (2011.01) | |

(52) U.S. Cl.
CPC ............. *A61K 9/5146* (2013.01); *A61K 9/06* (2013.01); *A61K 45/06* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | |
|---|---|---|
| 2004/0197416 A1 | 10/2004 | Simonnet et al. |
| 2008/0226739 A1 | 9/2008 | Wood et al. |
| 2015/0045419 A1 | 2/2015 | Lam et al. |
| 2016/0008282 A1 | 1/2016 | Hong et al. |
| 2018/0177892 A1 | 6/2018 | Mao et al. |

FOREIGN PATENT DOCUMENTS

| | | |
|---|---|---|
| CN | 103087311 A | 5/2013 |
| CN | 103748142 A | 4/2014 |
| JP | 2010065067 A | 3/2010 |
| WO | WO 2011/123591 A1 | 10/2011 |
| WO | WO 2012/158622 A2 | 11/2012 |

OTHER PUBLICATIONS

Andren et al (Multifunctional Poly(ethylene glycol): Synthesis, Characterization, and Potential Applications of Dendritic-Linear-Dendritic Block Copolymer Hybrids. Macromolecules 2013, 46, 3726-3736) (Year: 2013).*
Hoare (Hydrogels in drug delivery: Progress and challenges. Polymer 49 (2008) 1993-2007) (Year: 2008).*
Chang et al (Synthesis and Photophysical Characterization of Amphiphilic Dendritic-Linear-Dendritic Block Copolymers. Journal of Polymer Science: Part A: Polymer Chemistry, vol. 39, 918-926 (2001)) (Year: 2001).*
Talelli et al (Core-Crosslinked Polymeric Micelles: Principles, Preparation, Biomedical Applications and Clinical Translation. Nano Today. Feb. 1, 2015; 10(1): 93-117) (Year: 2015).*
Li et al (Mercaptan acids modified amphiphilic copolymers for efficientloading and release of doxorubicin. Colloids and Surfaces B: Biointerfaces 153 (2017) 220-228). (Year: 2017).*
Andren et al., "Multifunctional Poly(ethylene glycol): Synthesis, Characterization, and Potential Applications of Dendritic-Linear-Dendritic Block Copolymer Hybrids", Macromolecules, 2013, 46: 3726-3736.
Barrio et al., "Self-Assembly of Linear—Dendritic Diblock Copolymers: From Nanofibers to Polymersomes", Journal of the American Chemical Society, 2010, 132(11): 3762-3769.
Choi et al., "Telodendrimers for Physical Encapsulation and Covalent Linking of Individual or Combined Therapeutics", Molecular Pharmaceutics, 2017, 14: 2607-2615.
Mongkhontreerat et al., "Dendritic Hydrogels: From Exploring Various Crosslinking Chemistries to Introducing Functions and Naturally Abundant Resources", Journal of Polymer Science, Part A: Polymer Chemistry, 2015, 53: 2431-2439.
Olofsson et al., "Soft hydrogels from tetra-functional PEGs using UV-induced thiol-ene coupling chemistry: a structure-to-property study", RSC Advances, 2014, 4(57): 30118-30128.
Wang et al., "Approaches for the preparation of non-linear amphiphilic polymers and their applications to drug delivery", Advanced Drug Delivery Reviews, 2012, 64(9): 852-865.
Fan et al., "Nanogel Encapsulated Hydrogels as Advanced Wound Dressings for the Controlled Delivery of Antibiotics", Advanced Functional Materials, Nov. 2020, 31: 2006453, 11 pages.

(Continued)

*Primary Examiner* — Jake M Vu
(74) *Attorney, Agent, or Firm* — James S. Keddie; Bozicevic, Field & Francis LLP

(57) ABSTRACT

The present invention relates to a nanogel of nanoparticles. The nanoparticles comprise self-assembled dendritic containing polymers having at least one dendritic hydrophobic segment forming the core and at least one hydrophilic segment forming the shell.

17 Claims, 19 Drawing Sheets

(56) References Cited

OTHER PUBLICATIONS

Hui et al., "Preparation and Aggregation Behavior of Linear-Dendritic Amphiphilic Polymer and Micelles", Journal of East China University of Science and Technology (Natural Science Edition), 2016, 42(6): 800-807.

\* cited by examiner

| Name of hybrid dendritic material | Scaffold architectures | PEG [Da] | Generation | Mw [g/mol] | Hydrophobic region (wt%) | Hydrophilic region (wt%) |
|---|---|---|---|---|---|---|
| mn-PEG2K-G1-Allyl | LD / LD#6 | 2000 | G1 | 2281.33 | 12% | 88% |
| mn-PEG2K-G2-Allyl | LD / LD#6 | 2000 | G2 | 2677.77 | 25% | 75% |
| mn-PEG2K-G3-Allyl | LD / LD#6 | 2000 | G3 | 3470.65 | 42% | 58% |
| mn-PEG2K-G4-Allyl | LD / LD#6 | 2000 | G4 | 5056.41 | 60% | 40% |
| mn-PEG5K-G1-Allyl | LD / LD#6 | 5000 | G1 | 5281.33 | 5% | 95% |
| mn-PEG5K-G2-Allyl | LD / LD#6 | 5000 | G2 | 5677.77 | 12% | 88% |
| mn-PEG5K-G3-Allyl | LD / LD#6 | 5000 | G3 | 6470.65 | 23% | 77% |
| mn-PEG5K-G4-Allyl | LD / LD#6 | 5000 | G4 | 8056.41 | 38% | 62% |
| mn-PEG10K-G1-Allyl | LD / LD#6 | 10000 | G1 | 10281.33 | 3% | 97% |
| mn-PEG10K-G2-Allyl | LD / LD#6 | 10000 | G2 | 10677.77 | 6% | 94% |
| mn-PEG10K-G3-Allyl | LD / LD#6 | 10000 | G3 | 11470.65 | 13% | 87% |
| mn-PEG10K-G4-Allyl | LD / LD#6 | 10000 | G4 | 13056.41 | 23% | 77% |
| PEG2K-G1-Allyl | DLD / DLD#6 | 2000 | G1 | 2562.66 | 22% | 78% |
| PEG2K-G2-Allyl | DLD / DLD#6 | 2000 | G2 | 3355.54 | 40% | 60% |
| PEG2K-G3-Allyl | DLD / DLD#6 | 2000 | G3 | 4941.3 | 60% | 40% |
| PEG2K-G4-Allyl | DLD / DLD#6 | 2000 | G4 | 8112.82 | 75% | 25% |
| PEG6K-G1-Allyl | DLD / DLD#6 | 6000 | G1 | 6562.66 | 9% | 91% |
| PEG6K-G2-Allyl | DLD / DLD#6 | 6000 | G2 | 7355.54 | 18% | 82% |
| PEG6K-G3-Allyl | DLD / DLD#6 | 6000 | G3 | 8941.3 | 33% | 67% |
| PEG6K-G4-Allyl | DLD / DLD#6 | 6000 | G4 | 12112.82 | 50% | 50% |
| PEG10K-G1-Allyl | DLD / DLD#6 | 10000 | G1 | 10562.66 | 5% | 95% |
| PEG10K-G2-Allyl | DLD / DLD#6 | 10000 | G2 | 12941.3 | 23% | 77% |
| PEG10K-G4-Allyl | DLD / DLD#6 | 10000 | G4 | 16112.82 | 38% | 62% |
| PEG20K-G1-Allyl | DLD / DLD#6 | 20000 | G1 | 20562.66 | 3% | 97% |
| PEG20K-G2-Allyl | DLD / DLD#6 | 20000 | G2 | 21355.54 | 6% | 94% |
| PEG20K-G3-Allyl | DLD / DLD#6 | 20000 | G3 | 22941.3 | 13% | 87% |
| PEG20K-G4-Allyl | DLD / DLD#6 | 20000 | G4 | 26112.82 | 23% | 77% |

FIG. 3

DENDRITIC NANOGEL CARRIERS AND METHOD OF PRODUCTION

CROSS-REFERENCE TO RELATED APPLICATIONS

This application is a § 371 national phase of International Application No. PCT/SE2019/050745, filed on Aug. 13, 2019, which claims the benefit of Swedish Patent Application No. 1850975-2, filed on Aug. 13, 2018, which applications are incorporated by reference herein.

FIELD OF INVENTION

The present invention is directed to nanogels or dendritic nanogels (DNGs) carriers comprising dendritic hydrophobic segments and hydrophilic segments characterized in that being a self-assembled hybrid material between hydrophilic polyethylene glycol (PEG) and modified hydrophobic dendritic 2,2-Bis(hydroxymethyl)propionic acid (bis-MPA), subsequently cross-linked and characterized in that the core is either anionic or cationic, hydrophilic and/or hydrophobic. More particularly the invention relates to the use of said dendritic nanogel and corresponding formulations as therapeutic agents for example for the prevention and/or treatment of skin infections, burn wounds and lung infections.

BACKGROUND ART

Dendritic molecules or highly branched molecules such as dendrimers are a class of well-defined nanostructured macromolecules with narrow polydispersity or even monodispersity, and a multivalent surface amenable for further modifications. Dendrimers are extensively and continually investigated for biomedical applications such as gene therapy, drug delivery and bioimaging purposes. Dendrimers are versatile which allows conjugation, complexation, and/or encapsulation of multifunctional moieties. Functional groups may be arranged on the periphery of dendrimer acting as highly accessible handles for drug or other functional group attachments. Since the functionalities of the drugs and ligands are diverse, there is a need to explore various functional group presentations at the dendrimer surface. By using different functional moieties (drugs or imaging agents) onto a single dendrimer in a control way is difficult because all the peripheral groups of the symmetric dendrimer have the same reactivity. A suitable linker or spacer is required to react with the surface functionality of dendrimer, providing the flexibility to link multiple moieties such as drugs, imaging or targeting agents.

In the prior art it is well known the use of dendritic molecules/dendrimers as carriers for drug delivery. It is also known that low molecular weight peptide could be attached to a dendrimer in order to be carried to a specific target. Different type of "raw materials" can be used to produce a dendritic structure and several "strategies" can be used to attach or encapsulate peptides and polypeptides.

The use of functional dendritic structures based on aliphatic polyester building blocks to increase the efficiency of Antimicrobial peptides AMPs (Feliu et al. 2011), have a huge potential since they are commercially available, biocompatible, highly homogenous and can efficiently be tailored in terms of composition, hydrophilicity, size and geometry to efficiently encapsulate peptides with various properties.

Most biomedical applications of dendrimers have so far been focused on delivery of small molecular drugs, mainly directed towards oncological applications, such as delivery of the antracyline antibiotic doxorubicin used in breast cancer treatment, using the positively charged poly(amidoamine) PAMAM class of dendrimer. The commercial availability of dendrimers is currently increasing as a consequence of their potential as therapeutic vehicles in the field of nanomedicine (Rolland et al. 2009). To date, hyperbranched polymers have solely been commercially exploited in industrial large scale applications. For instance, hyperbranched Boltorn™ based on 2,2-bis(methylol) propionic acid (bis-MPA) facilitate the production of polyurethane car seats worldwide (Perstorp AB).

From the array of dendritic materials found in literature, the non-toxic and biocompatible bis-MPA based dendrimer belongs to one of the most promising scaffolds for biological applications (Feliu et al. 2012, Carlmark et. al 2013).

Resistance to traditional antibiotics is a rapidly increasing problem that in a few years could make infections impossible to treat and bring the state of medical care back to the pre-antibiotic era from the beginning of the last century. Antimicrobial peptides (AMPs) have a huge potential as new therapeutics against infectious diseases as they are less prone to induce resistance due to their fast and non-specific mechanism of action. Functional delivery systems that can be applied directly on the infected site will be developed for treatment of infections in skin and burn wounds, as well as lung infections caused by Methicillin-resistant *Staphylococcus aureus* (MRSA), *Pseudomonas aeruginosa* and *Mycobacterium tuberculosis* (MTB).

Although large efforts in research and development have been directed towards the area of AMPs, only a few candidates have reached later stages of clinical trials and to date no or only few product based on AMPs has reached the market (Pasupuleti et al., 2012). One of the main reasons is the challenges related to stability of peptides in the formulations and after administration, which leads to reduced efficiency (Eckert 2011). Proteolytic degradation and self-aggregation are typical problems observed with these compounds. In order to increase efficiency and stability, various approaches to modify the peptide structure have been employed. However, these challenges can be overcome by choosing novel formulation strategies. With this respect, nanotechnology offers a wide range of unexplored possibilities.

The unique properties of biodegradable, nanostructured materials, including large surface areas, smart size ranges that enables transport across physiological barriers, ease of engineering and functionalization, possibility for targeting to different organs as well as high loading capacity of actives and various approaches to control the release kinetics, have led to a significant increase in the interest of using nanoparticles in various drug delivery applications.

The patent application WO2011123591 (A1) provides a biocompatible nanosized hydrogel particles suitable for injectable delivery of therapeutic agents for treatment of diseases or disease states and also for bioimaging purposes. These nanoparticles, including crosslinked hydrogels of the modified asymmetric PAMAM dendrimers and other polymers, are biodegradable and release the therapeutic agent over an extended period of time. It is also disclosed an injectable hydrogel comprising: a crosslinked poly(amidoamine) dendrimer having at least two asymmetrical orthogonal chemoselective peripheral ends, at least one of said asymmetrical orthogonal ends being crosslinked to form a gel and at least one other of said asymmetrical orthogonal ends being conjugated to a chemical agent, Said patent application describes that the drug contained within the hydrogel can be a peptide and, in addition, it is described that hydrogels can be used for many different applications such as molecularly engineered scaffolds for controlled drug release, cellular delivery, tissue engineering and as wound dressings. However, PAMAM is not biocompatible and the degradation products are potentially toxic.

The patent application US2012040431 (A1) discloses a dendrimer molecule comprising surface carboxylic acid groups. Said application discloses a therapeutic-loaded polymer that is covalently attached to a low molecular weight peptide. The polymer can be usefully derivatized. It is claimed a method of preparing a modified dendrimer comprising the step of obtaining a dendrimer molecule comprising surface carboxylic acid groups. This patent application also discloses that the recognition moiety is selected from the group consisting of (i) a peptide comprising one or more hapten moieties; (ii) folic acid; (iii) a targeting peptide; (iv) biotin; (v) an oligonucleotide; (vi) an anchoring domain peptide; (vii) an antibody; and (viii) an antibody fragment.

The patent application WO2005009396 (A2) discloses the use of polypeptides to be used for the prevention and treatment of infections. However, it does not disclose an efficient way of delivering said polypeptides.

The patent application WO2012109121 (A1) discloses a delivery system emulsion-based wherein the emulsion comprises carbohydrate nanoparticles and bacteriocin are adsorbed on the nanoparticles surfaces. Said system is made of a nanoparticle comprising a carbohydrate carrier and a bacteriocin, wherein the bacteriocin comprises a peptide. In some embodiments this patent application describes an amphiphilic carbohydrate nanoparticle, phytoglycogen octenyl succinate (PG-OS), and used PG-OS-stabilized emulsion to deliver functional peptides with prolonged efficacy. The terms "phytoglycogen or glycogen-type material" refer to dendritic (i.e., highly branched) a-D-glucan and carbohydrate nanoparticles. In other embodiments, the nanocarriers used are negatively charged, phytoglycogen-based dendritic polysaccharides that adsorb positively charged nisin molecules via electrostatic interactions.

Hybrids between dendritic structures and linear segments, as those shown in FIG. 2, are well-known in the prior art (so-called linear-dendritic hybrids). The dendritic part can be varied in size by growing different generations i.e. G1, G2, G3 etc of which each generation is based on a number of monomers. The linear part can also be varied by varying the chain length, so that the molecular weight varies (2 kDa, 5 kDa, 10 kDa, 20 kDa etc.). Due to their amphiphilic nature, the structures can self-assemble in different ways, depending on solvent, temperature, drying method etc.

It is an object of the present invention to present a biocompatible carrier that may be adapted in order to encapsulate anionic, cationic, hydrophilic or hydrophobic cargo. The present carrier protects encapsulated peptides against chemical and enzymatic degradation. It is another object of the invention to avoid peptide self-assembly, as well as to target and control the release of actives peptides. The present invention provides nanogels that are monomodal or essentially monomodal with a low polydisperisty index (PDI).

Accordingly the present invention provides nanostructured materials, more specifically a nanogel suitable for release of AMPs, characterized in that they provide:

1) Improved chemical stability. Deamidation is a common problem for AMPs both in a regulatory and functional aspect. Incorporation of AMPs in the present nanogel is believe to reduce deamidation to different extent.

2) Triggered release. The present nanogel can enable triggered release of the peptides. This can be used for instance in response to bacterial enzymes present in high concentrations in infections/infected areas.

3) Controlled release. For some infectious conditions, both for lung and skin infections, a sustained release formulation of AMPs could be of interest. Although AMPs have a rapid bactericidal effect, sustained release of AMPs would be relevant to decrease dosing frequency. Furthermore, sustained release during pulmonary administration will enable a larger dose without causing toxicity due to the relatively high peptide concentration in the lung fluid during administration of the AMP formulation.

Controlled drug release is crucial for may diseases treatment. For cancer treatment, controlled drug release can not only reduce unwanted side-effects caused by the drugs but also can increase local drug concentration at tumor area and improve the therapeutic effect.

4) Improved functionality. The present nanogel can be used to induce smart functionalities to the formulations, for instance absorption of excess fluids in wounds, bioadhesivity to increase local bioavailability and improved hydration of skin during topical administration.

5) The size of the nanogel may be easily controlled and adapted by the length of the hydrophilic segment.

Furthermore, the present invention provides a simple and cheap way of preparing a nanogel that may function as a carrier for drugs.

SUMMARY OF INVENTION

In view of the above the present invention is directed to a nanogel and a method to produce said nanogel. The nanogel according to the invention comprises a polymer having hydrophobic and hydrophilic segments: wherein the hydrophilic segments are or comprise polyethylene glycol (PEG) molecules and the hydrophobic segments are modified dendritic 2,2-Bis(hydroxymethyl)propionic acid (bis-MPA) molecules where hydrophobic segments are modified with allyl groups.

In a first aspect the present invention relates to a nanogel according to claim 1.

In a second aspect the present invention relates to a pharmaceutical composition containing the nanogel according to present invention for use in topical drug delivery.

In a third aspect the present invention relates to a pharmaceutical composition containing the nanogel according to the present invention for use to treat infections selected from the group consisting of skin infections, burn wounds and lung infections.

In a fourth aspect the present invention relates to a method for preparing the nanogel according to the present invention wherein the method comprises the following steps:
  Production of hydrophobic segments and linear hydrophilic segments;
  Self-assembly of hydrophobic segments and linear hydrophilic segments into a hybrid dendritic material scaffold in the form of self-assembled core shell nanoparticles;
  Cross-linking of the nanoscale assembled scaffold, performed on available allyls, to obtain nanogel;
  Optionally post-functionalization of the nanogel to introduce desired functionality, such as anionic, cationic or hydrophobic moieties.

In a fifth aspect the present invention relates to an aqueous composition comprising the nanogel according to the present invention wherein the aqueous composition comprises 0.1 to 99.9 wt % of the nanogel.

In a sixth aspect the present invention relates to a nanogel comprising nanoparticles, individual and/or inter connected, having a core and a shell;
   wherein the nanoparticles comprise self-assembled dendritic containing polymers having at least one dendritic hydrophobic segment forming the core and at least one hydrophilic segment forming the shell;
   wherein the hydrophilic segment is or comprises polyethylene glycol (PEG) and the hydrophobic segments are dendritic 2,2-Bis(hydroxymethyl)propionic acid (bis-MPA) molecules modified with allyl groups;
   wherein the core of said nanoparticles is either anionic, cationic, hydrophilic and/or hydrophobic; and wherein the hydrophobic segments are crosslinked via said allyl groups.

In the present invention the core of the dendritic nanogel carrier is either anionic, cationic, hydrophilic or hydrophobic. According to the core charge, anionic drug or cationic drug or hydrophobic drug is loaded thereof.

In a preferred embodiment of the present invention the delivered active substances are AMPs.

The present invention provides also a formulation comprising a dendritic nanogel carrier delivered in the form of topical spray, gel, pulmonary aerosol.

All embodiments disclosed herein relates to all aspects of the invention unless otherwise stated.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 shows data about structures evaluated for formation of DNGs

DETAILED DESCRIPTION OF INVENTION

With reference to the cited drawings it is provided, in the following, a description of a nanogel or a dendritic nanogel carrier and the method for producing it, according to the present invention.

The structure of said nanogel comprises a dendritic containing polymer comprising dendritic segments that are hydrophobic and segments that are hydrophilic which are also preferably linear. Said dendritic segments and linear segments undergo a self-assembling mechanism followed by covalent cross-linking (inter connections) to produce nanogels. The nanogel may comprise water.

Figure 1:
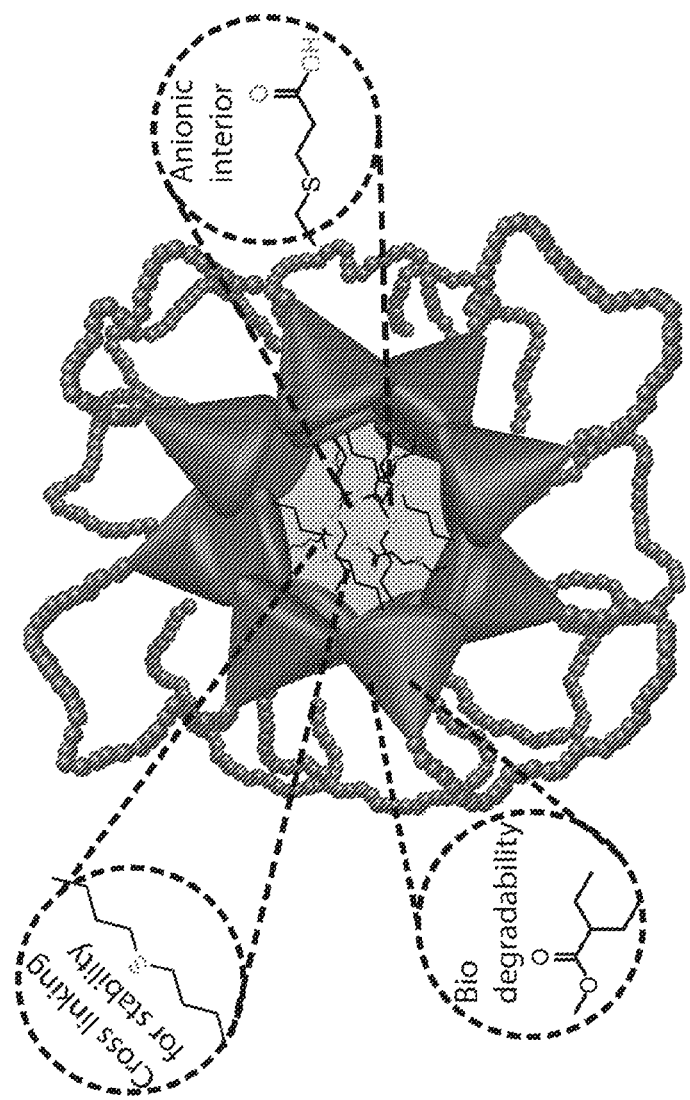
FIG. 1 shows a cross-linked biodegradable dendritic nanogels with anionic interior.

The present dendritic nanogels (DNGs) are formed by means of a self-assemble process of dendritic containing polymers into self-assembled core shell nanoparticles (NP), which subsequently are cross-linked to fixate the structure. The nanogels can be post-functionalized to introduce desired functionality, such as anionic, cationic, hydrophilic or hydrophobic moieties, FIG. 1. According to the present invention such dendritic containing polymer is a hybrid material comprising a hydrophilic region of polyethylene glycol (PEG) and a modified hydrophobic region of dendritic 2,2-Bis(hydroxymethyl)propionic acid (bis-MPA). The modification of the hydrophobic region is done by introduction of one or more allyl groups on the bis-MPA. The PEG may have a molecular weight of 1,000 g/mol to 20,000 g/mol such as 2,000 g/mol or higher, or 5,000 g/mol or higher, but 15,000 g/mol or less, or 10,000 g/mol or less. The PEG is preferably linear. The bis-MPA is bonded preferably directly to the PEG via an ester.

Figure 15:
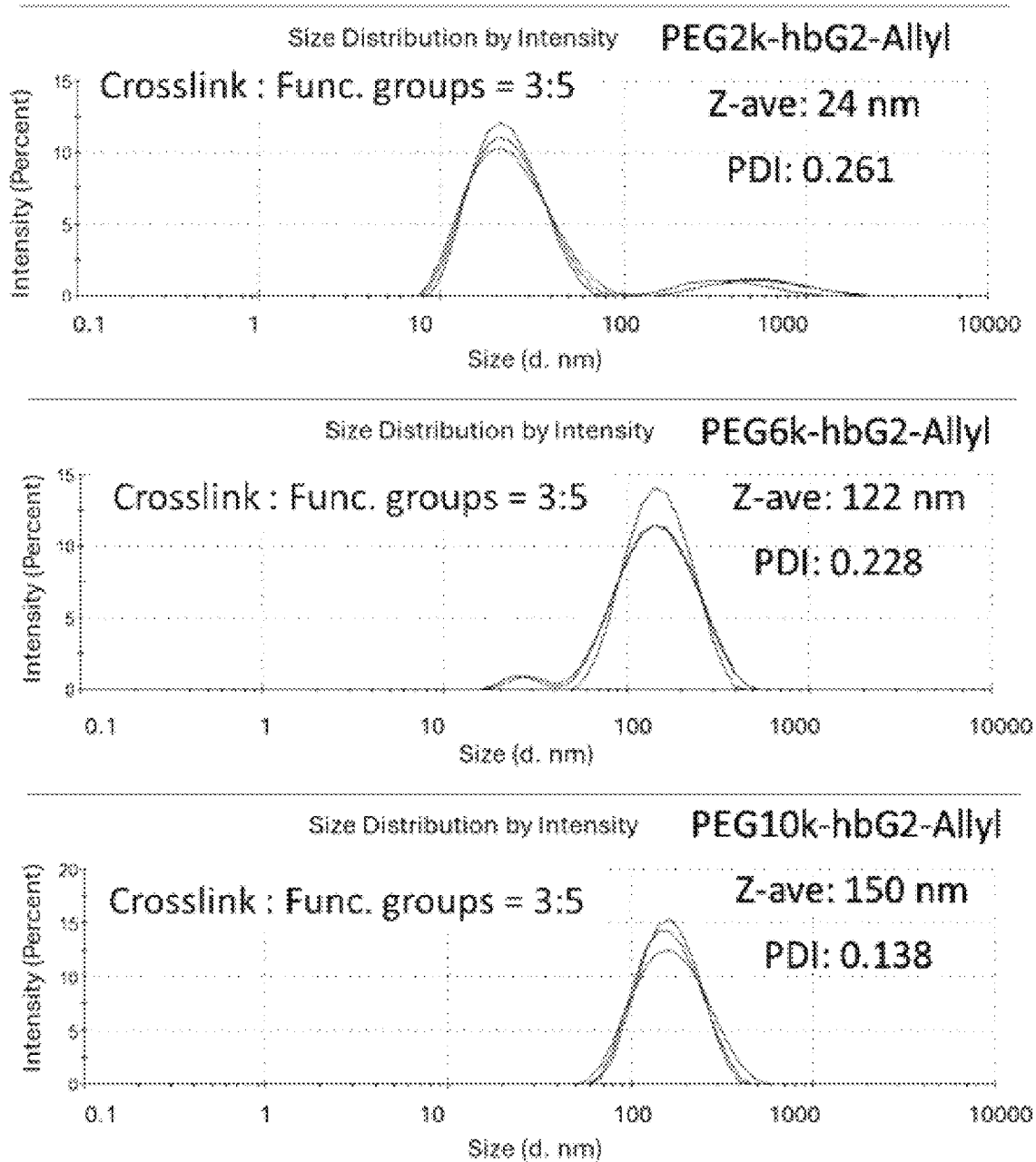
FIG. 15 DNGs with different sizes formed from DLD with different length of PEG. Crosslink:Functional group ratio were maintained at 3:5 in all cases.

The present inventors found that the size of the nanoparticle or nanogel can be adapted or controlled by the length of hydrophilic segments. For example using PEG with a molecular weight of 2,000 g/mol gave an average size (Z-average, ISO 22412) of 24 nm, while a PEG of 6,000 g/mol and 10,000 g/mol resulted in a Z-average of 122 nm and 150 nm respectively (FIG. 15). This is of interest since the body will take up smaller particles much faster than larger particles that instead remain circulating in the body. Thereby the uptake and release rate of the drug may be adapted.

Figure 2:
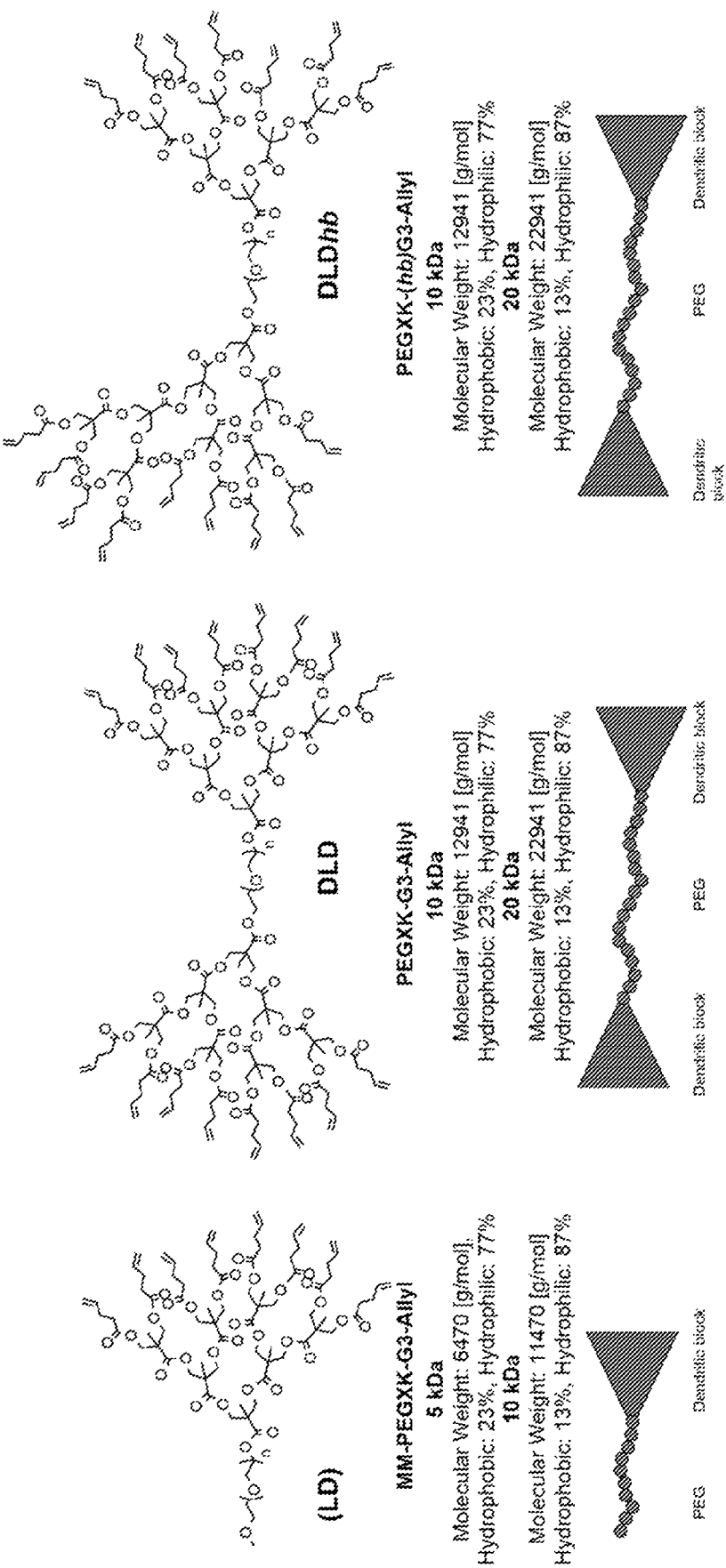
FIG. 2 shows a synthetically produced materials constituting of linear polyethylene glycol (PEG) and dendritic 2,2-Bis(hydroxymethyl) propionic acid (bis-MPA) with terminal allyls.

The above hybrid material or dendritic containing polymer can be produced using three different scaffold architectures, as showed in FIG. 2: a linear dendritic (LD), a dendritic linear dendritic (DLD), a dendritic linear dendritic hyperbranched (DLDhb) hybrids; wherein the linear poly ethylene glycol (PEG) block can have two different lengths. The DLDhb is characterized in that the hyper branched scaffold is not structurally perfect in comparison with LD and DLD. How close to the dendritic structure a hyperbranched structure is usually quantified by the degree of branching (DB). DB is defined as the ratio between perfect branches and the sum of all branches. The degree of branching was calculated using the Fréchet equation.

Quantification of terminal (T), linear (L) and dendritic (D) branched was conducted using quantitative carbon NMR. Using the integrals of the signals characteristic to the specific monomer units, the degree of branching (DB) was calculated from Formula 2.

$$DB = \frac{D+T}{D+T+L} \qquad \text{(Formula 2)}$$

Perfect dendritic DB=1
Hyperbranched<1

Preferably the DB is <1 i.e. the dendritic part is hyperbranched since it results in better nanogels, in comparison with perfect dendritic structures, where the nanogels are monomodal or essentially monomodal (single or narrow size distribution) with a low PDI.

Said hybrid materials are characterized in that having different relative percentages of hydrophilic and hydrophobic regions, as showed in the following FIG. 3.

Figure 4A:
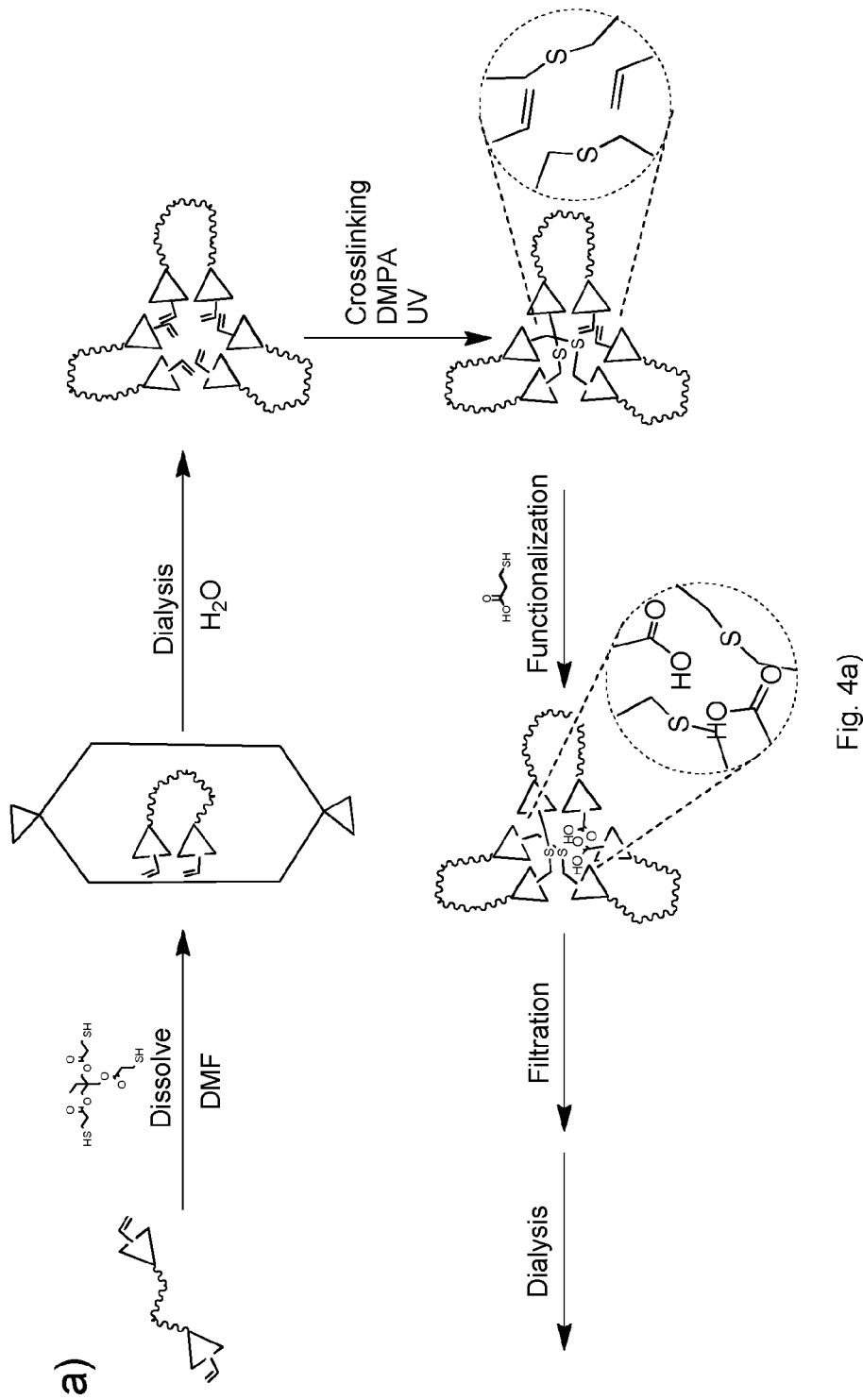
FIG. 4 shows self-assembly formation procedures: a) dialysis, b) thin film absorption. Each figure outlining the principle of the method in graphical terms.
Figure 4B:
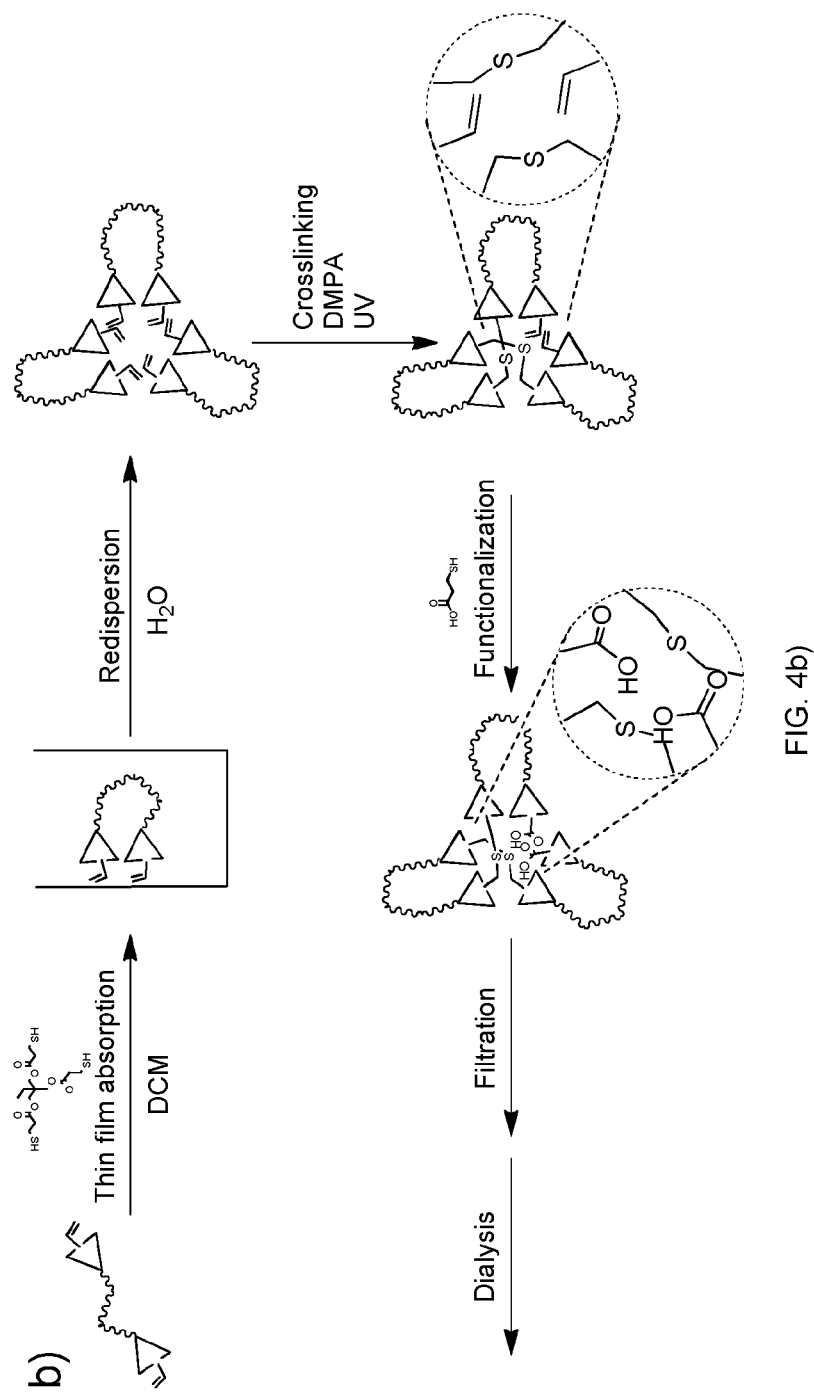
Figure 5A:
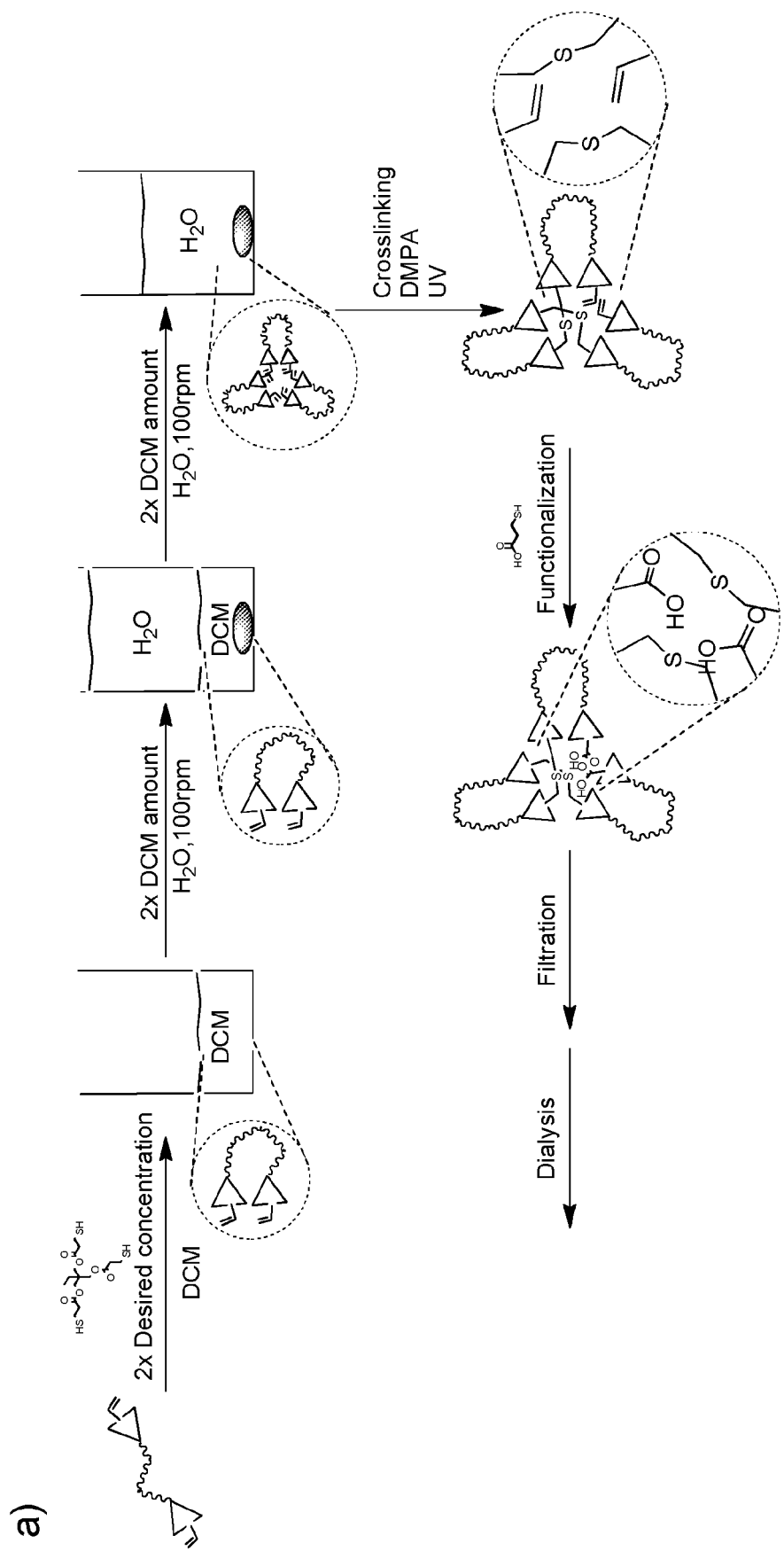
FIG. 5 shows self-assembly formation procedures: a) solvent exchange, b) micro dispersion. Each figure outlining the principle of the method in graphical terms.
Figure 5B:
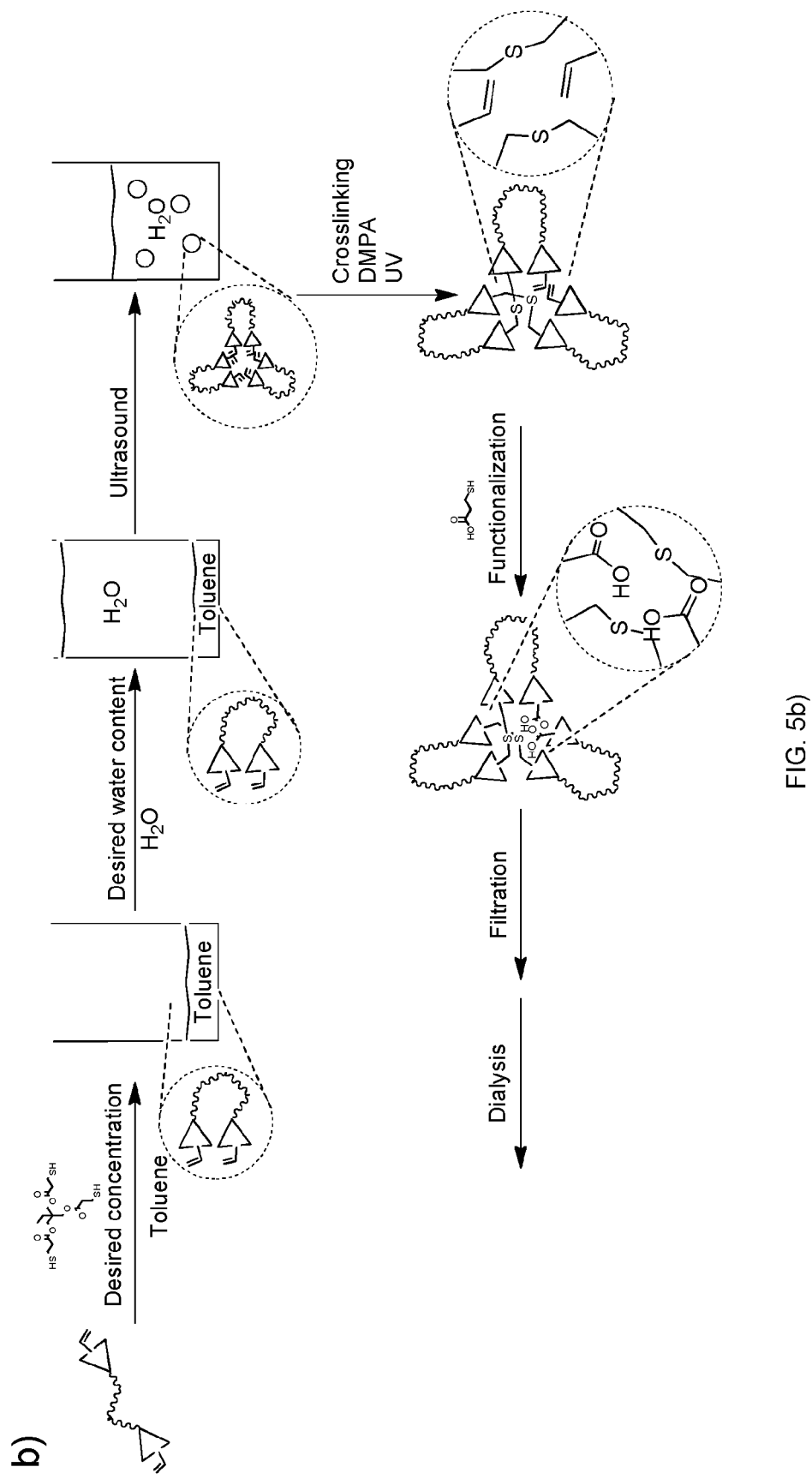

The self-assembly step of the dendritic hybrid materials into a scaffold can be realized using four different methods known from literature, as showed in FIGS. 4 and 5.

In a preferred realisation of the invention a thin film absorption method is used for the self-assembly step of the dendritic hybrid materials, as showed in FIG. 4*b*. In comparison with other methods of the prior art (FIGS. 4 and 5), the thin film absorption method is characterized by a superior self-assembly outcome, ease of use and convenient scalability. Said method consists of dissolving in a suitable container the dendritic containing polymer along with UV initiator and cross linker in a suitable solvent, for example dichloromethane (DCM), followed by slowly evaporating the solvent while twisting the container to coat a thin layer of polymer film onto the sides of the container. A suitable amount of water is then added to disperse the dendritic containing polymer forcing it to encircle the hydrophobic cross linker and initiator with the hydrophilic part of the molecule towards the water causing the formation of self-assembled core shell nanoparticles. The solution containing self-assembled NP constructs are then exposed to UV light causing radical crosslinking in the core, fixating the structure and thus preventing disassembly.

Functionalization of the interior of said NP constructs may be conducted by adding an excess of intended functionality along with UV-Initiator dissolved in water and again exposing the mixture to UV irradiation. Purification may then be performed using dialysis against THF for one hour and then milli-Q water for 24 hours with water.

The self-assembly of the dendritic containing polymer shows best performance with a relative molecular weight percentage (wt %) of hydrophilic segment between 70-90 wt % and with a hydrophobic segment between 10-30 wt %. This means for example that 70-90% of the total molecular weight of the linear-dendritic polymer may be the hydrophilic segments such as PEG and 10-30% may be the hydrophobic segments such as bis-MPA and pheripheral groups.

In a preferred embodiment 87 w hydrophilic and 13 wt % hydrophobic ratio offered superior properties in terms of self-assembly using the thin film absorption method without the crosslinking and functionalization. Accordingly, different types of scaffolds can be prepared using said preferred hydrophobic to hydrophilic ratio, for example: L087/13, DLD87/13, DLDhb87/13.

Figure 6A:
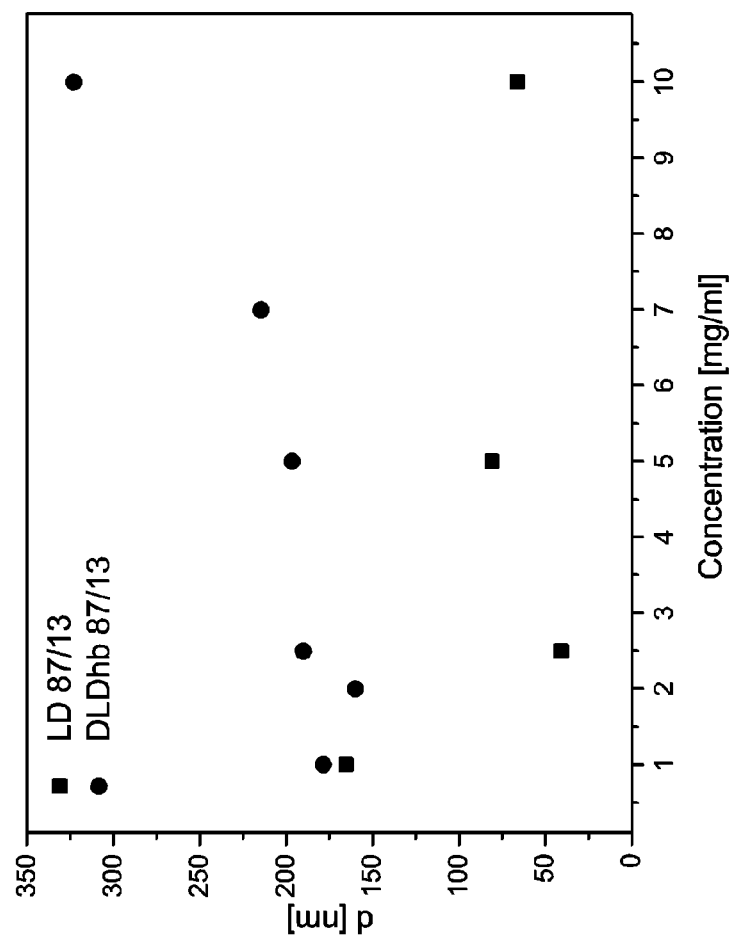
FIG. 6 shows DLS concentration study of DLDhb87/13 and LD87/13: a) Hydrodynamic diameter plotted against concentration, b) 100—peak area vs concentration defining the precentral aggregation in the system.
Figure 6B:
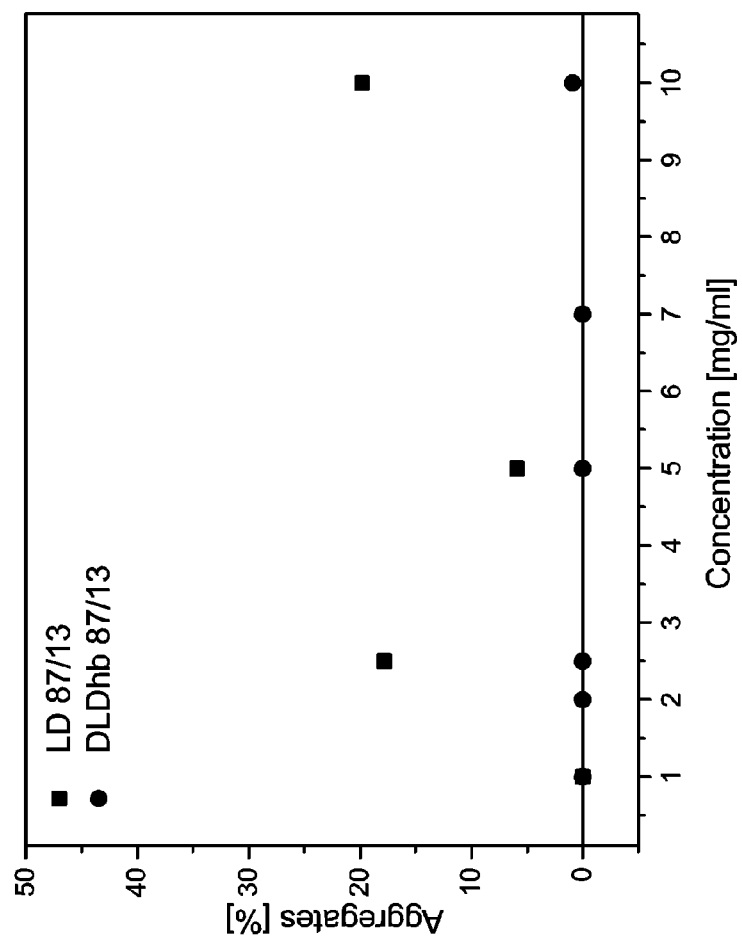

Surprisingly the DLDhb87/13 scaffold shows superior control over the self-assembled adducts as showed in FIG. 6 where the size of the constructs and the amount of aggregates are plotted against the respective scaffolds and concentration. It is showed that the hyperbranched DLDhb87/13 material provides a more controlled and defined NP in comparison with other scaffolds with the same hydrophobic to hydrophilic ratio. In FIG. 6 *b* it is showed that LD87/13 scaffold provides more aggregates while DLDhb87/13 scaffold provides more control over self-assembled constructs. Size wise, relating to the nanogel or the self assembly, the LD87/13 is smaller than the DLDhb87/13 system offering sizes down to 50 nm in diameter while the larger DLDhb87/13 system offers sizes between 180 and 300 nm FIG. 6 *a*.

Different PEG lengths and dendritic generation can be used for the formation of DNGs. In a preferred embodiment the dendritic segment is of second generation (G2) or of third generation (G3). In a more preferred embodiment the PEG has a molecular weight of 2000-10000 g/mol and the dendritic segment is G2. In another more preferred embodiment the PEG has a molecular weight of 10000-20000 g/mol and the dendritic segment is G3. These embodiments results in nanogels that are monomodal or essentially monomodal (singe) or narrow size distribution) and with a low PDI such as 0.3 or lower preferably 0.1 or lower, FIG. 7.

In one embodiment the size distribution of the nanogel is essentially monomodal or monomodal, FIG. 7*b*. In another embodiment the nanogel has a polydispersity index (PDI) of 0.3 or lower preferably 0.25 or lower, or more preferably 0.20 or lower, or more preferably 0.1 or lower.

The crosslinking ratio in the nanogel may be 15-65 mol % i.e. 15-65 mol % of the allyl groups are used in the crosslinking. In a preferred embodiment the crosslinking ratio is 30-65 mol % more preferably 50-60 mol %.

Figure 7:
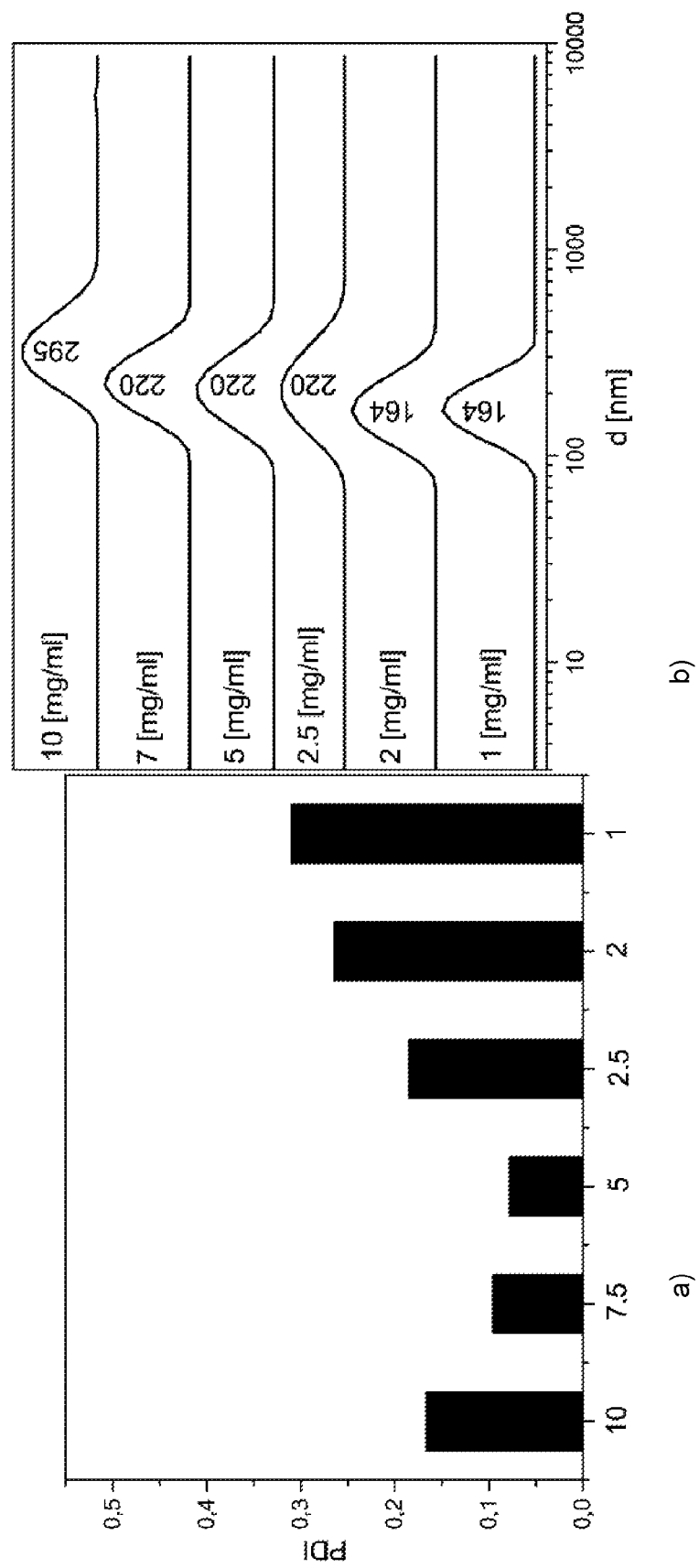
FIG. 7 shows DLS concentration study of DLDhb87/13: a) PDI against concentration, b) DLS traces at all measured concentrations.

In FIG. 7 it is shown the optimal concentration for formation of NP, where concentration is plotted against the dispersity index. It is apparent that the lowest PDI, that is the narrowest size distribution and the most uniform NP, is attained at a concentration of 5 mg/ml as confirmed by the DLS traces in FIG. 7*b*. At a concentration of 10 mg/ml a small amount of aggregation of nanogels is seen in the intensity trace otherwise no aggregates can be seen for any concentration. In a preferred embodiment the concentration is 3-6 mg/nil more preferably 5 mg/ml. In a preferred embodiment the pharmaceutical composition according to the present invention comprises 3-6 mg/ml or more preferably 5 mg/ml of nanogel.

The formation of the dendritic nanogel, by means of a cross-linking step of the nanoscale assembled scaffold, provides a contraction from 295 nm to 220 nm (measured by DLS and TEM), probably caused by the constriction of covalent bonds forming in the core of the DNG. Cross-linking increases the stability with the current date passing 300 days. Addition of THF and acetone to the cross-linked system did not cause disassembly in the cross-linked system while in the non-cross-linked system it caused complete disassembly also indicating crosslinks were formed.

Figure 8:
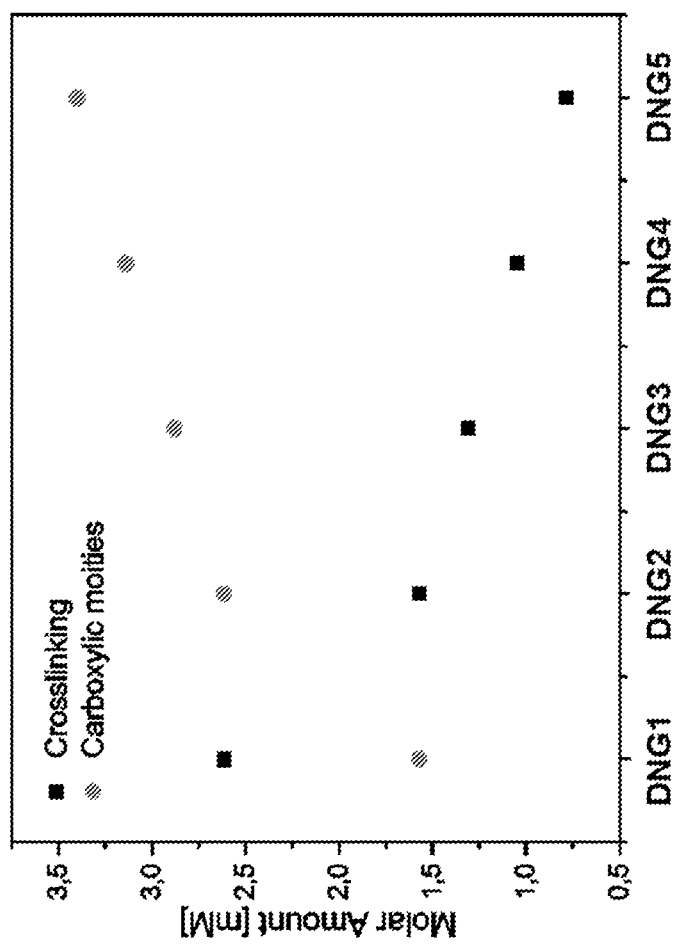
FIG. 8 shows molar of amine and molar of crosslinks for each of the DNG formulations.

Crosslinking step can be performed on a different percentage of available allyls, for example between 15 mol % and 65 mol %. In preferred realisations of the present invention crosslinking is produced on the following percentage of available allyls: 18.25 mol %; 25.00 mol %; 31.25 mol %; 37.50 mol %; 62.50 mol % A graphical representation of degree of crosslinking as well as molar amount of anionic moieties produced can be seen in FIG. 8. The gels are abbreviated dendritic nano gel (DNG) and with a number from 1 to 5. In Table 1 the ratios of crosslinking for the different DNGs can be seen.

TABLE 1

Cross-linking ratios for DNGs

| | Name | | | | |
|---|---|---|---|---|---|
| | DNG1 | DNG2 | DNG3 | DNG4 | DNG5 |
| Cross-linking [mol %] | 62.5 | 37.5 | 31.25 | 25 | 18.75 |
| Remaining allyls [mol %] | 37.5 | 62.5 | 68.75 | 75 | 81.25 |

The crosslink may be obtained using thiolene chemistry forming a sulphur bond or sulphur bridge. The crosslinking may be performed using mercapto propionic acid or cysteamine and a di- or trifunctional thiol. The crosslinking may result in a thioether linkage.

The allyl group may be any suitable C3 or longer alkyl group comprising an unsaturation. In one embodiment the allyl group is a C3 to C6 group (—CH2-CH═CH2 to —(CH2)4-CH═CH2). In another embodiment the allyl group is a C5 group (—(CH2)3—CH═CH2). The C5 group may be obtained by modifying using 4-pentenoic acid. Longer chain length in the allyl group increases the hydrophobicity in the hydrophobic segment.

DNGs offer several advantages as carrier, a large batch can be produced with a predetermined cross-linking degree. Then smaller batches can be functionalized to display anionic, cationic and hydrophobic core characteristics. The covalent attachment in the core of a fluorescent dye in combination with previously mentioned core characteristics is also possible. The core characteristics can be altered to optimally suit the intended cargo using various degrees of anionic, cationic, hydrophobic or a combination of moieties. Each batch would be otherwise identical since the "naked" cross-linked scaffold is from the same batch. Any thiol functional moiety can potentially be used to provide function or characteristics to the core and any thiol molecule with a number of thiols equal to or greater then three can be used as crosslinker. Fluorescent tags with a thiol functionality could be incorporated in the core to provide traceability to the scaffold. The modular nature of the DNGs with their vast possibilities for modification of the core characteristics offer the possibility to tailor the system to carry or encapsulate a wide variety of cargoes, for example: cationic or anionic molecules such as cationic drug loading, anionic drug loading; or hydrophobic or hydrophilic drug loading.

Encapsulation of Cationic Substances

Wherein the nanogel encapsulates a cargo that are cationic drugs, DNGs are accordingly modified to show anionic characteristics in the core by means of thiol-ene chemistry of appropriately cross-linked DNG with mercapto propionic acid.

Cargoes include cationic peptides, cationic proteins, cationic antigens and cationic synthetic molecules such as doxorubicin among many others.

Peptide loading is done by considering the charge of the peptide and the charge of the DNG. Peptide amount with equal or lower total charge than the charge of the DNG can be loaded into the system.

In a preferred embodiment the antimicrobial peptide loaded to the carrier is DPK-060 for the treatment of skin and soft tissue infections (SSTI).

Higher peptide concentrations display more pronounced aggregation than at lower peptide concentrations. Interestingly, no significant change in z-potential was observed upon DPK-060 loading suggesting that the gel structure contains a charged core screened from the surroundings by the linear PEG structure.

In another preferred embodiment the antimicrobial peptide loaded to the carrier is LL-37, a widely used AMP for a broad range of bacteria and also towards others pathogens (fungi, viruses).

The effect of nanoformulated AMPs (which are cationic) were evaluated with state-of-the art in vitro models and in vivo models.

Encapsulation of anionic substances Wherein the cargoes are anionic drugs, DNGs are accordingly modified to show cationic characteristics in the core by means of a functionalization performed using cysteamine or similar molecules thereof.

Cargoes include SI-RNA, anionic peptides, anionic proteins, anionic antigens and anionic synthetic molecules such as diclofenac, salicylic and ibuprofen acid among many others.

Loading is done by considering the charge of the drug and the charge of the DNG. Drug amount with equal or lower total charge than the charge of the DNG can be loaded into the system.

Encapsulation of hydrophobic substances Wherein the cargoes are hydrophobic drugs, DNGs can be used without modification since the residual allyls unused when cross-linking is performed, as well as the dendritic block, are hydrophobic. if a more hydrophobic nature is desired hexanethiol can for example be used to functionalize the core.

Cargoes include doxorubicin, cisplatin, gemcitabine, erlotinib, fluorouracil, mitoxantrone, irinotecan, Idarubicin, triptolite, paclitaxel among many other drugs that are hydrophobic in nature.

Loading is preformed by dissolving hydrophobic drug in a suitable solvent together with the freezedried DNG. Followed by the addition of water or buffer. The organic solvent is then allowed to evaporate completely, the excess drug can be purified by cassette dialysis.

Figure 14:
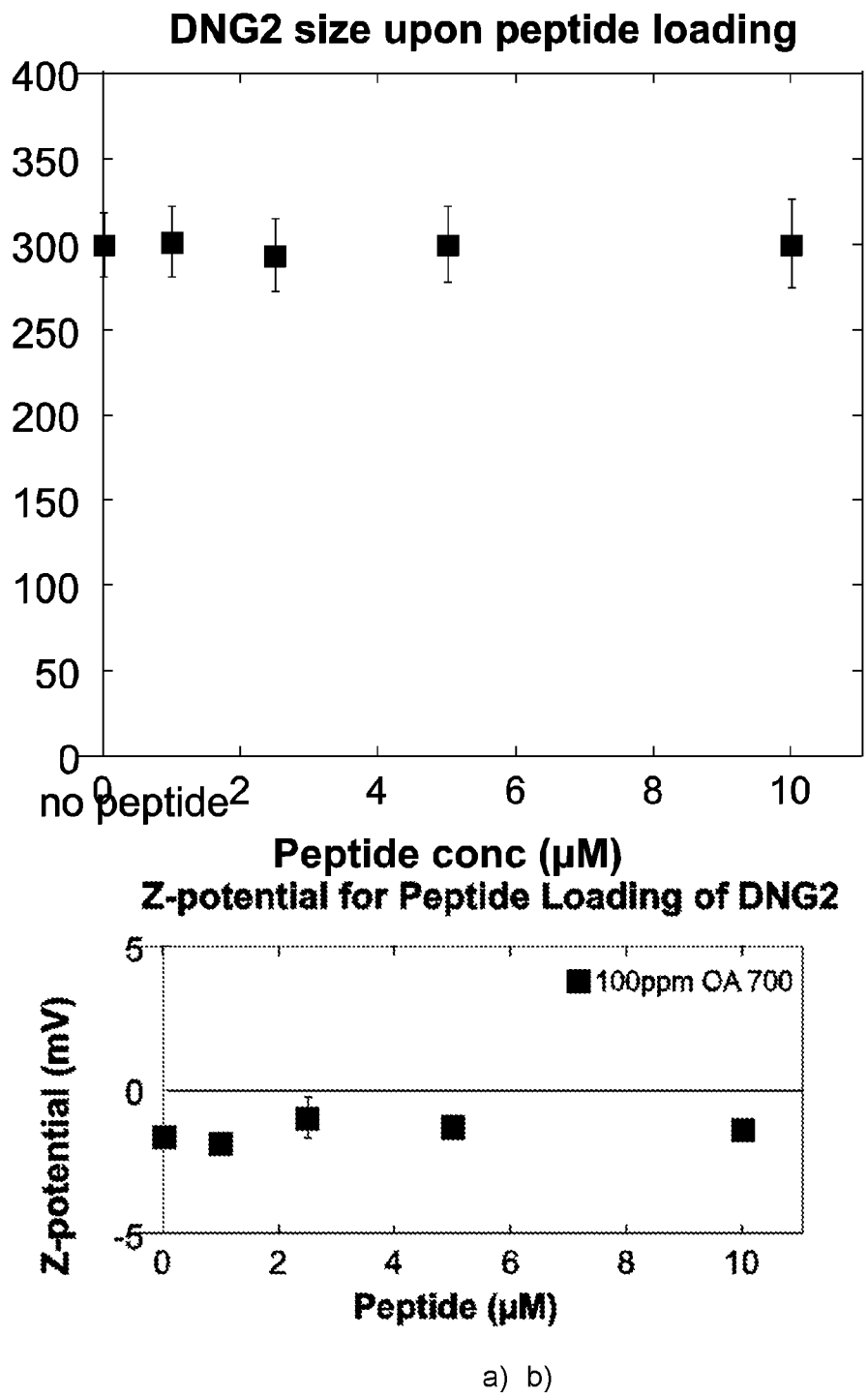
FIG. 14 shows dendritic nanogel size (a) and z-potential (b) as determined by DLS at different peptide loading in μM.

In a preferred embodiment the hydrophobic drug loaded is doxorubicine. FIG. 14 shows the release of said drug other time in the case of four samples: free DCX, DNG1, DNG2 and DNG5. Slow release characteristics can be seen where a release of approximately 50 wt % can be seen almost linearly after 96 h for ONG 1, 2 and 5.

The dendritic nanogels are all capable of both encapsulating and delivering target peptides, as evidenced by release studies monitored by confocal microscopy.

The present invention provides also a formulation comprising a dendritic nanogel carrier delivered in the form of topical spray, gel, pulmonary aerosol.

Example 1. General Synthesis Procedure of Dendritic Nanogel (DNG) Using DLDhb87/13 System PEG20K-G3-Allyl (200 mg, 8.75 µmol), Trimethylolpropane tris(3-mercaptopropionate) (TMP-SH) (10, 6, 5, 4, 3, eq/allyl for DNG 1, 2, 3, 4, 5 respectively) and 2,2-Dimethoxy-2-phenylacetophenone (DMPA) (10 wt %) was dissolved in DCM (4 mL) in a round bottom flask. The solvent was slowly evaporated under reduced pressure to form a thin transparent film. water (40 mL) was added to the flask and the flask was vortexed for 1 minute and submerged in an ultrasound bath (35 kHz) for 15 minutes. A sample was taken for size and 1H-NMR analysis. Resulting colloidal dispersion was exposed to UV light under constant stirring for 60 minutes (dosage=1526 J/mm2) (UVP Blak-Ray UV Benchtop Lamps, P/N: 95-00127-20M, 665 nm, 230V, 50 Hz). A sample was taken for size and 1H-NMR analysis. Mercapto propionic acid (30, 50, 55, 60, 65 eq/allyl for DNG 1, 2, 3, 4, 5 respectively) along with DMPA (10 wt %) dissolved in two mL of THF was added. The sample was vortexed for 1 minute and submerged in an ultrasound bath (35 kHz) for 15 minutes and subsequently exposed to UV light under constant stirring for 60 minutes (dosage=1526 J/mm2) (UVP Blak-Ray UV Benchtop Lamps, PIN: 95-00127-20M, 665 nm, 230V, 50 Hz). A sample was taken for size and 1H-NMR analysis (size: 190 nm, conversion allyls: (100 mol %)), The liquid was poured in to a dialysis membrane and dialyzed against THF: H2O (2:3), (1:3) and then water changing solvent with even intervals: 1, 1, 1, 2, 3, 15, 1 hours. Resulting slightly cloudy liquid was freeze dried to attain product as a fluffy cloud like solid (200 mg).

Example 2. General Synthesis of MM-PEGXK-G3-0H (LD) and PEGXK-G3-OH (DLD)

Refer to the following publication by Ihre et. α13; different mPEG (Mw=5 000, 10 000 g/mol) and PEG (Mw=10 000 and 20 000 g/mol) were used for fabrication of MM-PEG5K-G3-OH, MM-PEG10K-G3-OH, PEG10K-G3-OH and PEG20K-G3-OH, respectively.

Example 3. General Synthesis of PEGXK-(Hb)G3-OH (DLDhb)

The synthesis was based on polycondensation between PEG and Bis-MPA. PEG was added in a two necked round bottom flask equipped with argon inlet, magnetic stirrer and distillation equipment and heated to 130° C. Every sixty minutes bis-MPA equivalent to one increase in dendritic generation was added along with pTSA, (wt % pTSA based bis-MPA added; 1.5 wt % PEG2K, 5 wt % PEG6K and 5 wt % PEG20K). During addition of bis-MPA, argon was flushed through the reaction vessel. When the desired generation had been reached one additional hour of argon flushing was applied after which vacuum was induced in the reaction vessel for 18 hours. The resin was extracted from the reaction vessel by dissolution in DCM and consecutively precipitated in ether two times and subsequent dried on high vacuum. Generation 2 to 7 (G2-7) were synthesized according to the same reaction scheme for two different PEG (Mw=10 000 and 20 000 g/mol) for the fabrication of PEG10K-(hb)G3-OH and PEG20K-(hb)G3-OH, respectively (reference is made to Andrén et. AI).

Example 4. General Synthesis of MM-PEGXK-G3-Allyl, PEGXK-G3-Allyl and PEGXK-(hb)G3-Allyl Amphiphile was dissolved in pyridine (3 eq./OH) and DCM (10 ml) in a round bottom flask equipped with magnetic stirrer. DMAP (0.2 eq./OH) was added and the reaction was cooled to 0° C. using an ice bath. 4-Pentanoic anhydride (1.2 eq./OH) dissolved in 5 mL of DCM was slowly added over a period of 30 minutes. Reaction was allowed to proceed overnight and progression was monitored by 130-NMR by confirming the presence of the anhydride peak at 170.2 ppm. The crude reaction was precipitated in ether (1 L) and white powder collected; re dissolved in DCM and re precipitated in cold ether (1 L). Product was collected as a white powder.

Example 5. Full Conversion of Allyls in a Dendritic Nanogel Carrier

Figure 9:
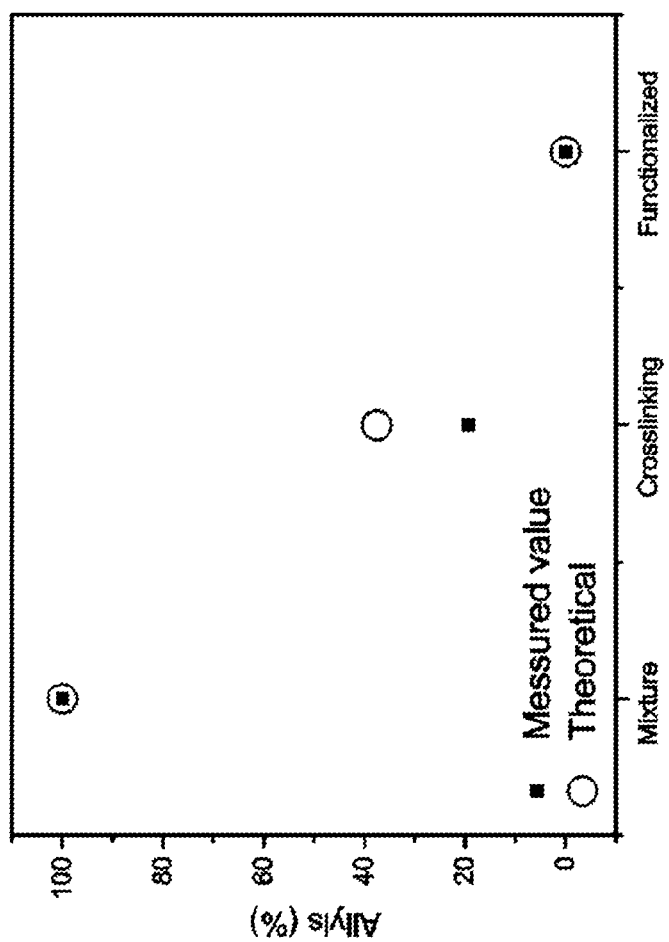
FIG. 9 shows conversion of allyls in percent going through self-assembly, crosslinking and functionalization of DNG2.
Figure 10:
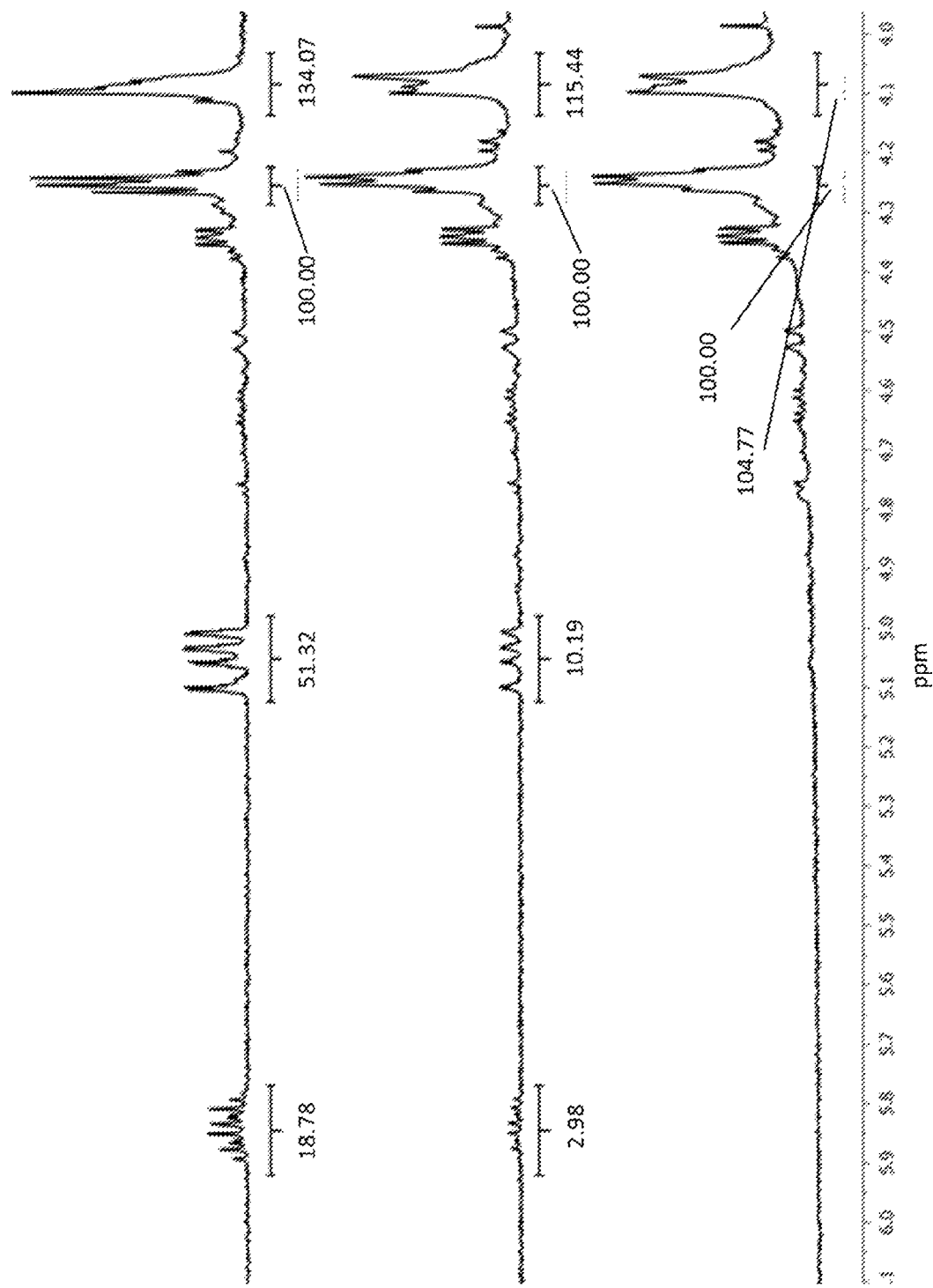
FIG. 10 $^1$H-NMR zoom of allyl specific region for freeze-dried DNG2 (right).

To ensure full conversion of the remaining allyls freeze-drying of DNG2 was preformed and allyl presence was investigated by NMR spectroscopy. In FIG. 10 (to the right) the spectra can be seen with complete disappearance of signal associated with allyls after functionalization, indicating full conversion to carboxylic interior. Since a core-shell structure is formed some degree of shielding of the desired structure can be expected causing the amount of allyls to be slightly underestimated (see FIG. 9). The crosslinking step may be done as previously described and resulting in different crosslinking ratios as seen in Table 1.

Figure 11:
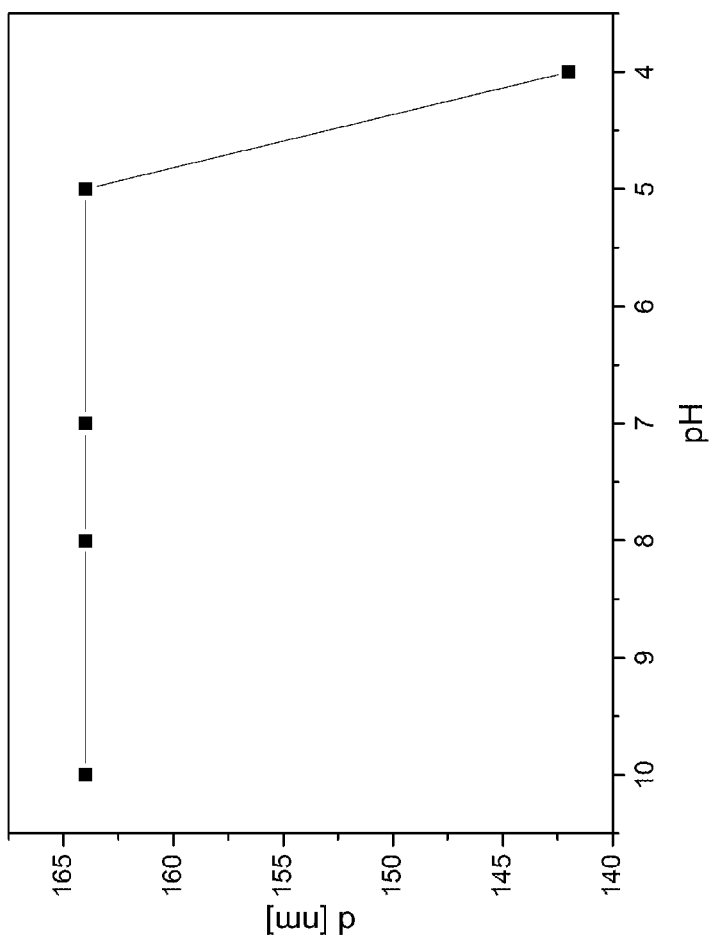
FIG. 11 shows size as measured by DLS of DNG2 as a function of pH.

The stability and appearance at different pH was investigated for DNG2. A small pH dependent contraction can be seen for DNG2 at PH 4. Indications showing that the interior is indeed anionic can be seen as an affect to alterations in the exterior pH, FIG. 11.

Figure 12:
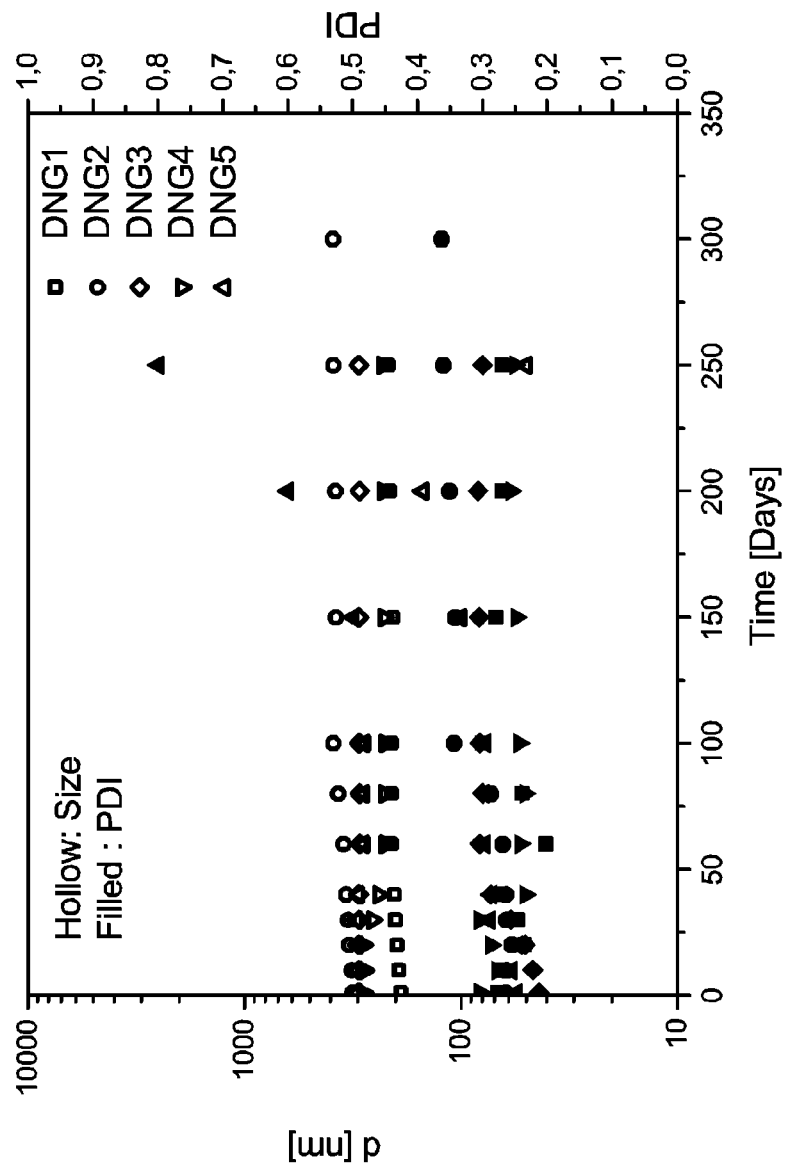
FIG. 12 shows size and PDI recorded using DLS for DNGs at room temperature in PBS.

The stability of the DNGs has been assed using DLS, the size and polydispersity index (PDI) was recorded for systems stored in milli-Q water at room temperature after a dilution in milli-Q water, FIG. 12. DNG 5 with the lowest crosslinking density displays some degree of instability where spectra can no longer be recorded with satisfactory results after 150 days. The rest of the DNGs appears to be quite stable even after almost 300 days of storage at room temperature.

Figure 13:
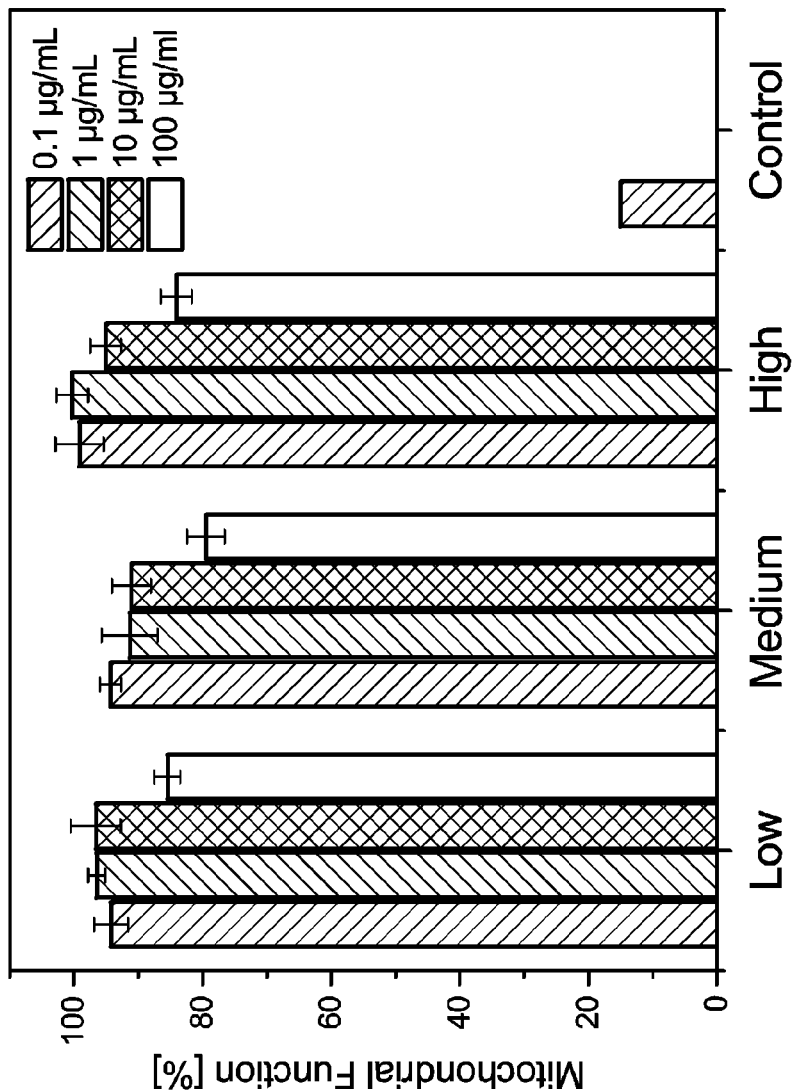
FIG. 13 shows mitochondrial function on human dermal fiberoblasts (HDF) as measured by 3-(4,5-Dimethylthiazol-2-yl)-2,5-diphenyltetrazolium bromide (MTT) assay with a 72 h incubation time. DMSO 10 vol % was used as positive control.

The DNGs are inherently non-toxic, below a MTI assay was preformed to evaluate the toxicity of DNG 1,2,3 modified to display anionic interior can be seen, FIG. 13.

The subject-matter of the invention is susceptible of numerous modifications and variations, without departing from the inventive concept as expressed in the accompanying claims.

All the above-described details may furthermore be replaced with other technically equivalent elements, and the materials may be different according to the single needs, without departing from the scope of protection of the present invention.

Although the present invention has been described with particular reference to the accompanying drawings, the reference numbers used in the description and in the claims are used to improve the intelligibility of the invention and do not represent any limitation to the scope of protection claimed. Example 6

Different nanogels were prepared according to the method disclosed in Example 1.

| Materials | Structure | Z-average (size by DLS) | PDI |
|---|---|---|---|
| PEG10k-hbG2-Allyl | DLD hyperbranched | 150 | 0.203 |
| PEG10k-hbG3-Allyl | DLD hyperbranched | 200 | 0.210 |
| PEG10k-G2-Allyl | DLD dendrons | 255 | 0.265 |
| PEG10k-G3-Allyl | DLD dendrons | 2714 | 1 |

Example 7

Figure 16:
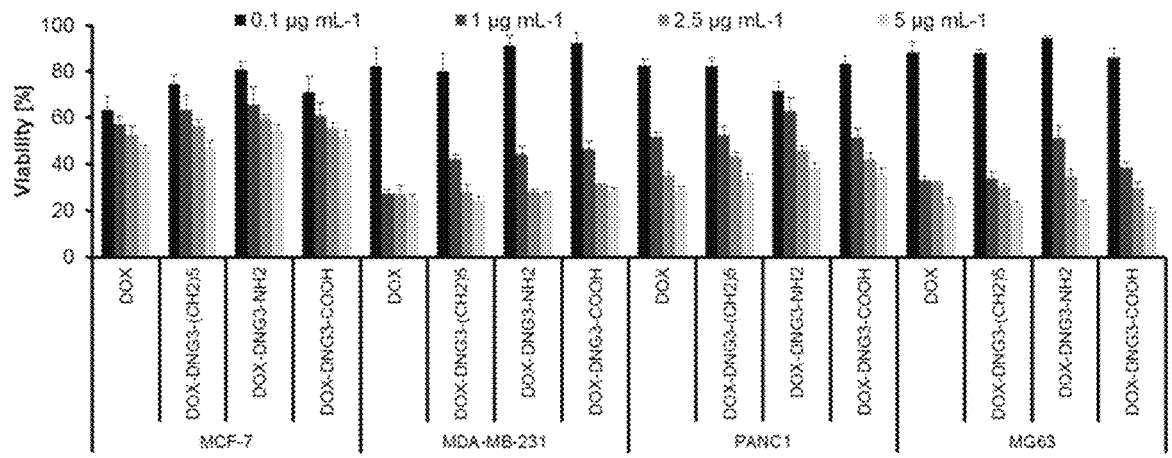
FIG. 16 discloses nanogel according to the present invention maintains or even improves the DOX efficacy towards a panel of cancer cells. AlamarBlue assay was used to evaluate the cytotoxicity induced by free DOX and DOX-DNGs against a panel of cancer cell lines with 72 h incubation.

FIG. 16: Doxorubicin (DOX) loaded DNGs showed similar or improved anticancer efficacy as free DOX.

Figure 17:
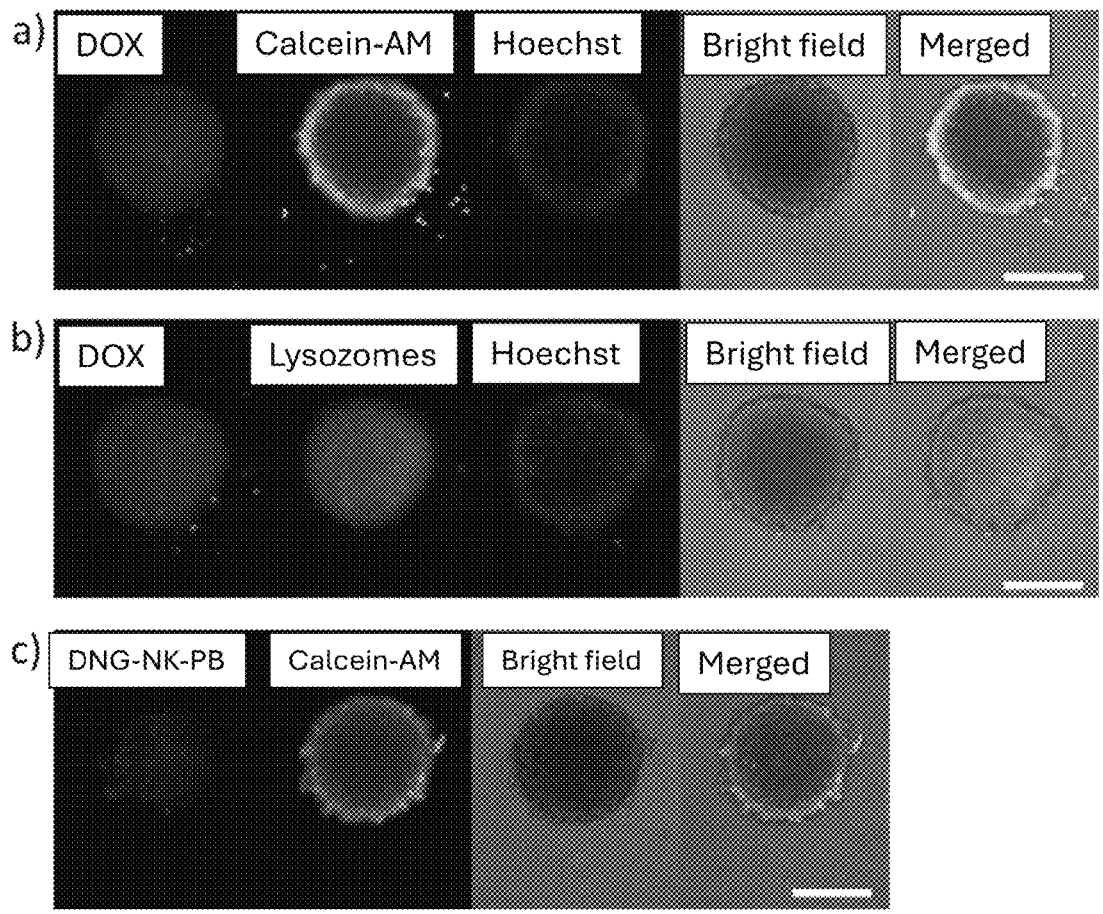
FIG. 17 Colocalization study on a 3D spheroid model. a,b) Colocalization study of DOX-DNG3—NH2 on 3D PANC1 spheroids. DOX signal was represented by red fluorescence; green fluorescence indicates (in a) Calcein-AM labeled living cells or (in b) lysoTracker DND-26 labeled lysosomes in cytoplasm; nuclei were stained with Hoechst 33342 and represented as blue signal. c) Colocalization study of pacific blue labeled DNG-NH2 (DNGNH-PB) on 3D PANC1 spheroids. Blue fluorescence represents DNG-NH-PB and green fluorescence indicates Calcein-AM labeled living cells. Scale bar=100 μm.

FIG. 17: (a-b) DOX loaded in DNG (red) can be delivered into 3D tumor model and distributed in both nuclei (blue) and cytoplasma (green). And (c) pure DNG labeled with blue fluorescent dyes can be also uptake into 3D tumor. Together (a-c) we know that DNG can be uptake into 3D tumor and deliver drug into 3D tumor.

The invention claimed is:

1. A nanogel comprising nanoparticles, individual and/or inter connected, having a core and a shell;
   wherein the nanoparticles comprise self-assembled dendritic polymers having at least two hydrophobic segments that are dendritic and at least one linear segment that is hydrophilic, wherein:
   the degree of branching of the hydrophobic segments is <1;
   the core of the nanoparticles comprises hydrophobic segments and the shell of the nanoparticles comprises hydrophilic segments;
   the hydrophilic segment comprises polyethylene glycol (PEG) having a molecular weight in the range of 5,000 g/mol to 20,000 g/mol and the hydrophobic segments are second to fourth generation dendritic 2,2-Bis(hydroxymethyl)propionic acid (bis-MPA) modified with allyl groups;
   the core of said nanoparticles is either anionic, cationic, hydrophilic and/or hydrophobic; and
   the hydrophobic segments are crosslinked via said allyl groups.

2. The nanogel according to claim 1 wherein 70-90% of the total molecular weight of the polymer is the hydrophilic segments and 10-30% of the total molecular weight of the polymer is the hydrophobic segments.

3. The nanogel according to claim 2 wherein the relative percentage of dendritic hydrophilic segments is 85-90 and the relative percentage of hydrophobic segments is 10-15 wt %.

4. The nanogel according to claim 1 wherein the cross-linking of the hydrophobic segments is via a thiol-ene reaction.

5. The nanogel according to claim 1 comprising a fluorescent tag to provide traceability.

6. The nanogel according to claim 1 wherein an anionic or cationic core is obtained by cross-linking said nanogel with mercapto propionic acid or cysteamine respectively and a di- or trifunctional thiol.

7. The nanogel according to claim 1 wherein the nanoparticle encapsulates cationic molecules selected from the group consisting of doxorubicin, cisplatin, gemcitabine, erlotinib, fluorouracil, mitoxantrone, irinotecan, Idarubicin, triptolite, and paclitaxel.

8. The nanogel according to any one of claim 1 wherein the nanoparticle encapsulates cationic molecules wherein the cationic molecules are selected from the group consisting of cationic peptides, cationic proteins, cationic antigens and cationic synthetic molecules.

9. The nanogel according to claim 1 wherein the nanoparticle encapsulates anionic molecules selected from the group consisting of SI-RNA, anionic peptides, anionic proteins, anionic antigens and anionic synthetic molecules.

10. The nanogel according to claim 9 wherein said anionic synthetic molecule is diclofenac, salicylic and ibuprofen acid.

11. The nanogel according to claim 1 wherein the allyl group is a C3-C6 allyl group.

12. A method comprising topically administering a pharmaceutical composition containing the nanogel according to claim 1 to a patient.

13. The method of claim 12, wherein the patient has a skin infection, burn wound or lung infection.

14. A method for producing the nanogel according to claim 1 comprising the following steps:
   producing of hydrophobic segments and linear hydrophilic segments;
   self-assembling hydrophobic segments and linear hydrophilic segments into a hybrid dendritic material scaffold in the form of self-assembled core shell nanoparticles;
   cross-linking of the nanoscale assembled scaffold, performed on available allyls, to obtain nanogel;
   optionally post-functionalizing the nanogel to introduce desired functionality.

15. An aqueous composition comprising the nanogel according to claim 1 wherein the aqueous composition comprises 0.1 to 99.9 wt % of the nanogel.

16. The pharmaceutical composition according to claim 12, wherein the concentration of the nanogel is 3-6 mg/ml.

17. The nanogel according to claim 1 wherein the nanogel is crosslinked using mercapto propionic acid, cysteamine or a di- or trifunctional thiol.

* * * * *